United States Patent
Oza et al.

(10) Patent No.: US 6,528,569 B1
(45) Date of Patent: Mar. 4, 2003

(54) SOLID WATER-SOLUBLE OR WATER-DISPERSIBLE COMPOSITIONS

(75) Inventors: Mrinalini Sachin Oza, Maidstone (GB); Rowena Roshanthi Landham, Maidstone (GB)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 09/674,386

(22) PCT Filed: May 17, 1999

(86) PCT No.: PCT/GB99/01559

§ 371 (c)(1),
(2), (4) Date: Oct. 30, 2000

(87) PCT Pub. No.: WO99/59407

PCT Pub. Date: Nov. 25, 1999

(30) Foreign Application Priority Data

May 20, 1998 (GB) .............................................. 9810861

(51) Int. Cl.[7] .............................. C08K 3/34; C08K 1/00; C08K 3/00; C05F 11/00; A01N 25/00
(52) U.S. Cl. ........................... 524/442; 524/35; 524/47; 524/444; 524/448; 524/449; 71/13; 71/27; 71/64.01
(58) Field of Search .............................. 524/35, 47, 442, 524/444, 448, 449; 71/13, 27, 64.01

(56) References Cited

U.S. PATENT DOCUMENTS 3,299,566 A * 1/1967 MacMullen
4,045,204 A * 8/1977 Matsunaga et al.
4,065,287 A * 12/1977 Roth
4,936,901 A * 6/1990 Surgant, Sr. et al.
5,378,751 A * 1/1995 Deibig et al.
5,766,615 A * 6/1998 Narayanan
5,998,536 A * 12/1999 Bertry et al.

FOREIGN PATENT DOCUMENTS

| GB | 2095558 | * | 10/1982 |
| WO | 82-03747 | * | 11/1982 |
| WO | 93/23999 | * | 12/1993 |
| WO | 94/23573 | * | 10/1994 |
| WO | 96/03038 | * | 2/1996 |

* cited by examiner

Primary Examiner—Tae H. Yoon

(57) ABSTRACT

The invention provides processes for producing solid, water-soluble or water-dispersible compositions comprising non film-forming materials, such as water-soluble agrochemical electrolytes, supported by film-forming polymers. The water-soluble agrochemical electrolytes can be salts of glyphosate. The processes comprise (i) preparing film-forming aqueous media containing (a) film-forming polymers; (b) water-soluble materials which are non film-forming; (c) water-miscible solvents in which the film-forming polymers are soluble and, optionally, (d) solid fillers, and thereafter (ii) drying the film-forming aqueous media to form the solid compositions. The invention also provides compositions produced by these processes.

24 Claims, No Drawings

SOLID WATER-SOLUBLE OR WATER-DISPERSIBLE COMPOSITIONS

RELATED APPLICATION

This application is a §371 of PCT/GB99/01559 filed May 17, 1999, which claims priority to GB 9810861.6 filed May 20, 1998.

This invention relates to a solid composition and to a process for preparing a solid composition and in particular to a process for preparing a solid, water-soluble or water-dispersible composition containing a water-soluble material which is not film-forming and a film-forming water soluble material.

Film-forming polymers are used in a number of industries to provide a solid polymer medium within which a second non film-forming component may be supported. Typical of such applications is the casting of an aqueous solution of the film-forming polymer to form polymer sheets (tapes) or flakes.

Thus for example in WO 93/23999 there is disclosed a packaging for storing and releasing incompatible crop protection materials in which a chemical is "encapsulated" or supported in a water-soluble polymer film.

Such processes typically involve as a first step dissolving a film-forming polymer in water to form an aqueous film-forming medium in which a material to be supported is dissolved or suspended. The film-forming medium is then for example cast onto a suitable substrate and dried to form a solid tape containing the material to be supported. Under certain conditions the tape may loose coherence during drying to form flakes. Alternatively, the film-forming medium can be dried to produce granules, agglomerates or powders.

We have found however that problems may arise when the non film-forming material to be supported is itself water-soluble, particularly if it is a strong electrolyte. Specifically, we have found that the presence of a water-soluble electrolyte in an aqueous solution of a film-forming polymer tends to interact adversely with the polymer at the relatively high polymer concentration required to provide adequate film-forming properties. As a result the film-forming polymer may be thrown out of solution as a rubbery deposit, and even quite small concentrations of water-soluble electrolyte may have a deleterious effect on the film-forming properties and homogeneity of the medium. The problem is exacerbated if the water-soluble electrolyte is hygroscopic such that even if a solid composition can be formed, it tends to pick up water causing the film-forming polymer component to become sticky.

According to the present invention there is provided a process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer (b) a water soluble material which is non film-forming and (c) a water-miscible solvent in which the film-forming polymer is soluble and thereafter (ii) drying the film-forming aqueous medium to form the solid composition.

Whilst the process of the present invention may be applied to any water-soluble material which is not film-forming and which is suitable for being supported in a solid composition of a film-forming polymer, it is of particular relevance when the water-soluble supported material is a strong electrolyte and even more particularly when the water-soluble supported material, in its dry form, is hygroscopic. Typical strong electrolytes are salts, for example inorganic salts or salts of an organic acid or base. The scope of the present invention is not restricted to a water-soluble supported material having a specific utility, although it is illustrated herein with reference to a water-soluble supported material having utility in the agrochemical field, either as an active agrochemical or as an agrochemical adjuvant. Typical examples of water-soluble active agrochemicals which are strong electrolytes are salts of glyphosate, including without limitation the trimethylsulphonium salt, the isopropylamine salt, the sodium salt, the potassium salt and the ammonium salt and bipyridylium salts such as paraquat dichloride, glufosinate and fomesafen.

Typical examples of agrochemical adjuvants which are strong electrolytes are organic or inorganic salts such as ammonium sulphate. The process of the present invention provides a convenient method of obtaining a solid formulation of an agrochemical or an agrochemical adjuvant or an agrochemical formulation containing both active agrochemical and adjuvant having advantages in respect of handling, storage, transportation and reduced container contamination. Typical solid formulations of the present invention such as tapes or flakes provide a convenient delivery vehicle for the agrochemical or agrochemical formulation and may be arranged for example such that a single unit dose of agrochemical is contained in a unit dose package, for example in a conventional unit dose package or in water-soluble sachet packaging. If the process of the present invention is used to form a cast tape, the tape may be cut to provide a length corresponding to a desired dose. Furthermore we have found that the process of the present invention may be used to provide solid compositions containing a higher loading of agrochemical or agrochemical adjuvant than would be possible in the absence of water-miscible solvent. In certain circumstances the process of the present invention may be used to provide a solid composition containing an agrochemical formulation whose individual components are incompatible if used in the form of an aqueous liquid concentrate. Thus for example it may be possible to use a higher content of an adjuvant such as ammonium sulphate than would be compatible as an aqueous liquid concentrate formulation of an agrochemical.

In a preferred embodiment of the present invention, the solid composition additionally contains a solid filler.

According to a further aspect of the present invention there is provided a process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer, (b) a water soluble material which is non film-forming, (c) a water-miscible solvent in which the film-forming polymer is soluble and (d) a solid filler and thereafter (ii) drying the film-forming aqueous medium to form the solid composition.

The solid filler is preferably a water-dispersible solid inorganic or organic filler such as calcium silicate, magnesium silicate (talc), sodium aluminium silicate, silica, mica, cellulosic fibre such as wood fibre, starch and diatomaceous earth. It is especially preferred that a highly adsorptive filler is used, for example a filler having a high surface area for example a surface area greater than 5 $m^2/g$ and preferably greater than 80 $m^2/g$. As a specific example of a suitable filler there may be mentioned CALFLO E (CALFLO is a trade mark World Minerals), a calcium silicate filler having a surface area of about 100 m²/g.

The term "film-forming" polymer includes any polymer which is capable of providing film-forming properties in the presence of water. The film-forming polymer will generally be water-soluble but could also provide a film-forming aqueous medium in which the film-forming polymer is present in the form of a dispersion, and in particular a colloidal dispersion or in the form of a sol or in the form of a solution containing some dispersed material.

Suitable film-forming polymers include both synthetic and natural polymers such as polyvinylpyrrolidone, polyvinyl alcohol, partially hydrolysed polyvinyl acetate, modified polyvinylpyrrolidone such as a polyvinylpyrrolidone/vinyl acetate copolymer, polyethylene oxides, ethylene/maleic anhydride copolymer, methyl vinyl ether-maleic anhydride copolymer, water-soluble cellulose such as carboxymethylcellulose, water-soluble polyamides or polyesters, copolymers and homopolymers of acrylic acids, starches, natural gums such as alginates, dextrins and proteins such as gelatins and caseins. Mixtures of such film-forming polymers may also be used. Polyvinylpyrrolidone is an especially preferred film-forming polymer.

The water miscible solvent in which the film-forming polymer is soluble will vary depending on the nature of the film-forming polymer. Suitable solvents for use with polyvinylpyrrolidone or vinylpyrrolidone copolymers such as vinlyacetate/vinylpyrrolidone copolymers include alcohols, for example linear or branched chain primary or secondary alcohols containing from 1 to 6 carbon atoms, ethylene glycol, propionic acid, methylcyclohexanone, methylene dichloride, N-methyl-2-pyrrolidone, and diethanolamine. Ethanol is an especially convenient solvent in view of its ready availability and low cost. Suitable solvents for use with carboxycellulose include for example glacial acetic acid. Suitable solvents for use with other film-forming polymers will readily occur to those skilled in the art.

The film-forming aqueous medium is preferably formed by first dissolving the film-forming polymer in the relevant water-miscible solvent. To avoid unnecessary reduction in the film-forning properties of the polymer, it is preferred to dissolve the film-forming polymer in the minimum quantity of solvent. The solubility of the film-forming polymer in any given solvent may be readily determined, and illustrative proportions are given in the Examples. The solid filler, if used, is conveniently dispersed in the solution of the film-forming polymer in the solvent and the resultant mixture is then added to an aqueous solution of the water-soluble material which is not film-forming, for example to an aqueous solution of an agrochemical. Alternative orders of addition are equally acceptable but dispersion of the solid filler in the solution of the film-forming polymer in the solvent is generally easier than dispersion in the aqueous solution of the agrochemical.

The resultant film-forming aqueous medium is then dried to form a solid composition. The water-miscible solvent for the film-forming polymer is preferably volatile such that at least a major proportion of the solvent is removed with the water during drying. Whilst not being limited to any one particular theory, it is believed that preferred solvents such as ethanol may actually assist the removal of water (even in the presence of a hygroscopic water-soluble electrolyte), for example through the formation of an azeotrope.

The physical form of the resultant solid composition will depend on the exact manner of drying of the film-forming aqueous medium and a wide variety of processes may be used to provide a wide range of solid products. For example simple drying of the film-forming aqueous medium will generally form a powder or agglomerate. Greater control of the formation of a powder or granule product may be obtained by spray drying or freeze drying of the film-forming aqueous medium. The film-forming medium may be partially or wholly formed into fibres, for example by being extruded into a fast-moving stream of air, and the resultant solid composition may take the form of fibres or of a uniform particulate composition resulting from the breaking up of such fibres on further drying. The film forming aqueous medium can also be applied on an anti-adherent, rotating drum surface by means of a roller and subsequently dried by hot air to yield dry flakes. Alternatively the film-forming material may be cast in the form of a film onto a substrate, for example a conveyor belt, from which it is preferably removed after drying.

The casting of the film-forming aqueous medium onto a substrate may take place using conventional techniques such as tape casting. In tape casting, a film is formed on a substrate and the thickness is adjusted to that required using a device such as a "doctor blade" which defines a predetermined space between the surface of the substrate and the knife of the doctor blade. The substrate is conveniently a flat, planar surface but may also if desired possess indentations to provide appropriate corresponding patterning on the surface on the film. Similarly, the "doctor blade" may have a contoured knife to provide corresponding patterning on the top surface of the film. In the extreme, the substrate may comprise one or more wells into which the film-forming aqueous medium is cast so that discrete pellets or tablets are formed on drying.

In commercial practice, it is normal to supply the film-forming medium from a reservoir and to form the film continuously, for example by the use of a moving belt as substrate or by movement of a reservoir and associated doctor blade relative to a stationary substrate. In commercial practice it is usually convenient to use a metal substrate although a plastics substrate may be used if desired.

The cast medium may be dried under atmospheric conditions but it is more conveniently dried at elevated temperature. In general it is sufficient to dry the cast medium at a temperature of from ambient to 100° C., for example from 40 to 60° C. It is to be understood that the drying process will not necessarily remove all traces of water and of the solvent for the film-forming polymer, and indeed a small proportion of residual water or solvent in the dry, cast product may have a beneficial plasticising effect. Typically levels of water in the range of 0.1 to 20% by weight are to be expected in the dry, cast product. Heating may be achieved for example by passing the cast medium into an oven or heated space or by applying heat to the substrate. Once the cast medium is dried, it may be removed from the substrate for subsequent use.

The cast medium may be removed from the substrate as a coherent sheet (a cast tape) and the coherent sheet may if desired subsequently be subdivided, for example by cutting, punching, or flexing to form flakes or shaped forms. Alternatively the proportions of the components of the film-forming medium, for example the content of the solid filler, may be selected such that the cast medium looses coherency during drying and cracks with the formation of flat flakes of product.

The thickness of the cast product, for example the cast tape or flakes, may be varied within wide limits according to the desired application. Typically the thickness of a cast tape or flakes varies between about 0.04 mm to 5 mm depending on the flexibility and other characteristics desired. If flakes are not formed directly, the dry tapes can be cut or fashioned to include a wide variety of shapes and designs, including for example discs, flakes, strips, tubes and spirals. The tape can be cut to provide a pre-determined metered dose of active ingredient which simplifies the formation of a dilute agrochemical spray for example. The tapes may also be embossed, corrugated or patterned to increase the surface area and may also carry printed information such as product and safety information.

For certain applications it may be desirable to protect the surface of the cast, dry product. The surface of the cast product may readily be protected by lamination or co-casting with a layer of water-soluble polymer which contains no active product and which may be the same as or different from the film-forming polymer. Alternatively, the cast, dry product may be housed in a water-soluble bag which may be manufactured from the same or different water-soluble polymer.

The proportions of the components of the solid composition formed by the process of the present invention may be varied widely depending on factors such as (a) the desired content of the active material in the solid composition (b) the process used to obtain the solid product and the desired properties of the aqueous film-forming medium and (c) the desired properties (such as dispersibility) of the resultant solid composition.

Thus for example if the film-forming aqueous medium is to be used to form a cast tape or cast flakes, a relatively higher film-forming level of polymer is likely to be required in the film-forming aqueous medium as compared with the film-forming aqueous medium used for spray-drying. Similarly a more coherent product is likely required if the final product is to be a cast tape rather than flakes. Such a coherent product is likely for example to require a relatively higher proportion of film-forming polymer as compared with the solid filler content. In general, sufficient of the film-forming polymer should be used to form a film-forming aqueous medium, by which is meant an aqueous medium having a suitable rheology and in particular a suitable viscosity for the drying process selected, for example for casting on a substrate. If there is insufficient polymer in solution, the aqueous medium will tend to run off the substrate and form too thin a film. If on the other hand too much polymer is present in the aqueous medium, it will not flow smoothly and the resultant film will not be self-levelling and uniform. The optimum concentration of polymer to provide an effective film-forming aqueous medium will vary depending on the exact nature and grade of polymer used but may be determined by simple and routine experimentation. Typical concentrations are illustrated in the Examples. Thus for example the concentration of the film-forming polymer in the film-forming aqueous medium is typically from 5 to 95% by weight, for example from 5 to 50% by weight.

As noted above, it is a particular advantage of the process of the present invention that a high loading of the water-soluble supported material may if desired be obtained in the solid composition. For example in favourable circumstances greater than about from 40% or 50% and even up to as high as 70% or more by weight of a water-soluble supported material such as an agrochemical active ingredient may be incorporated in the solid composition of the invention. This itself carries with it a further advantage in that potential problems of poor dispersion of the solid composition in water may be greatly reduced when a major proportion of the solid composition is the water-soluble agrochemical. It may thus for example be possible to use a film-forming polymer or other components which would otherwise give rise to dispersion problems if used at higher concentrations or if used in conjunction with water-insoluble components. It is of course possible to use lower proportions of water-soluble supported material, for example 20% or less by weight, if desired but some of the advantages of the present invention may not be so apparent in such products.

According to a further aspect of the present invention there is provided a solid, water-dispersible composition comprising a water-soluble agrochemical electrolyte, a film-forming polymer and a solid filler wherein the concentration of the water-soluble agrochemical electrolyte in the composition is greater than 60% and preferably greater than 70% by weight.

One skilled in the art will readily be able to determine appropriate proportions for each desired application but further detail is now given for the purposes of illustration only.

The proportion of polymer necessary to provide the required film-forming properties of the aqueous medium depends, at least in part, on the molecular weight of the polymer. We have found for example that polyvinylpyrrolidone is particularly suitable as a film-forming polymer which is commercially available in water-soluble or water dispersible grades having molecular weights in the range from about 8,000 to greater than 1,000,000 Dalton. A preferred grade of polyvinylpyrrolidone has a molecular weight in the range from 10,000 to 360,000 and in particular from 30,000 to 60,000. Polyvinylpyrrolidones having a molecular weight below about 30,000 can be used to form satisfactory cast tapes and flakes or other products, but a relatively large proportion of polymer is required to achieve a satisfactory film-forming aqueous medium with the consequence that the proportion of active supported material in the final product is undesirably reduced in favour of polymer. Similarly, polyvinylpyrrolidones having a molecular weight up to 360,000 may be used satisfactorily but the products tend to be sticky and, whilst the process of the present invention greatly reduces the risk of polymer coming out of solution in the presence of electrolyte, the use of very high molecular weight polymers might still give problems. As noted previously, any tendency to poor dissolution of the final product as a result of the use of a relatively high molecular weight polymer may be offset, at least in part, by the ability to increase the loading of the water-soluble active component and thus improve the dispersibility.

In general, we have found for example that for cast flake products, it is desirable to use a minimum of about 6% by weight of polyvinylpyrrolidone having a molecular weight of between about 30,000 and 50,000 to achieve coherent flakes. There is no real upper limit to the proportion of polyvinylpyrrolidone which may be used but generally there is little advantage in a product having high levels of film-forming polymer and low levels of supported material. The proportion of film-forming polymer in the final product is thus typically from 6% to 50% by weight.

We have found that the use of a solid filler provides a number of advantages and in particular avoids excessive stickiness in the product if for example a hygroscopic water-soluble electrolyte is supported by the film-forming polymer. Typically it is desirable for this reason to use at least 9% by weight and preferably at least about 20% by weight of solid filler in the final product. There is little advantage in a product having excessively high levels of solid filler, and the proportion of solid filler in the final product is thus typically from 9% to 50% by weight, for example from 20% to 30% by weight.

If desired, other components may be added to the film-forming aqueous medium. Thus for example it may be desirable, particularly if the cast product is to be a cast tape (a film), to include a plasticiser to improve the flexibility of the cast product. Suitable plasticisers include glycerols, $C_2$ to $C_6$ glycols and polyglycols such as polyethylene glycol, dialkyl phthalates such as dioctyl phthalate, sorbitol and triethanolamine or mixtures thereof. In addition to improving the flexibility of the product a plasticiser may also have an advantageous effect on the rate of dispersion of the dry, cast product in water. The proportion of plasticiser is preferably within the range 0 to 80% by weight, for example from 5 to 30% by weight relative to the film-forming polymer.

Surfactants may be added to the film-forming aqueous medium both to enhance the rate of dispersion of the dry product in water and also to affect the surface tension properties of the film-forming aqueous medium relative to a substrate on which it is cast. Thus for example a wetter may be added to ensure wetting of the substrate, for example if a plastics substrate is used. If it is desired to produce cast tapes rather than flakes, surfactants may also be added which modify the surface tension of the wet cast film and ensure that on drying the film reduces in thickness with minimum shrinkage in the plane of the substrate on which it is cast. A wide variety of surfactants may be used for these purposes and suitable examples will occur to one skilled in the art. Solid surfactants may be present in relatively high loading in the cast product and may be used for example to provide adjuvant properties in the final application, for example as a wetter in a spray solution for agrochemical use.

An antifoam agent may be added to prevent excessive aeration during mixing of the film-forming aqueous medium. A viscosity aid may be added if desired to modify the viscosity of the film-forming aqueous medium, for example to minimise any settling of the solid filler within the thickness of the wet film during drying. Suitable viscosity-modifying aids include alginates, starch, gelatin, natural gums, hydroxyethyl cellulose, methyl cellulose, silica and clays.

According to a further aspect of the present invention there is provided a solid water-soluble or water-dispersible composition whenever prepared by a method according to the present invention.

The invention is illustrated by the following Examples in which all parts and percentages are by weight unless otherwise stated.

EXAMPLE 1

Polyvinylpyrrolidone (5.0 g, molecular weight 24,000) was added to ethanol (11.7 g) and stirred manually until the polymer had dissolved. A high surface area calcium silicate filler (3.3 g; CALFLO E-CALFLO is a trade mark World Minerals) and glyphosate trimesium (10.4 g of an aqueous solution comprising 60.5% salt—41.7% glyphosate acid equivalent) were added to the polymer solution and mixed using a high speed mechanical stirrer over a period of 5 minutes until a homogeneous, viscous slurry was produced.

The viscous film-forming medium was cast onto a polymer film (polythene) as substrate using a casting devise known as a "doctor blade" set at a blade height of 1 mm. The cast tape was dried for 45 minutes in an oven maintained at 50° C. and then stripped from the substrate as a coherent sheet which was subsequently cut manually into flakes.

The tape cast product contained 43.1% glyphosate trimesium salt (29.7% glyphosate acid equivalent), 34.3% polyvinylpyrrolidone and 22.6% filler. The flakes had a thickness of 0.46 mm and showed excellent dispersion characteristics when added to water. The dispersion time as measured by the standard test given below was 72 seconds. When a sample of flakes was exposed to ambient conditions (22° C. temperature, 66% relative humidity) in an open petri dish for 5 days, it did not deliquesce.

The dispersion time of the solid was measured in a standard test by placing a square sample of known thickness measuring 10×10 mm in a mesh basket which was suspended below the surface of 500 ml of tap water (20° C.±1° C.) contained in a 600 ml glass beaker. The time for complete disintegration of the sample under conditions of no agitation was noted.

Comparison 1

The formulation procedure described in the above example was repeated with the exception that the ethanol was replaced with CIPAC Standard Hard Water D (11.7 g; 342 ppm hardness, $Ca^{2+}:Mg^{2+}=4:1$). The water, polymer and filler produced a homogenous mixture as before. However, addition of the water soluble salt (glyphosate trimesium active ingredient) resulted in the formation of a two-phase system which was not possible to homogenise. The mixture consisted of a liquid phase and an elastic-like solid phase. It was not possible to cast this mixture.

EXAMPLE 2

The procedure of Example 1 was repeated using ethanol (17.5 g), polyvinylpyrrolidone (7.5 g), CALFLO E (5.0 g) and the active ingredient glyphosate trimesium was replaced by 22.1 g of ammonium glyphosate (an aqueous solution containing 41.3% salt—37.5% glyphosate acid equivalent).

The resultant coherent solid contained 42.2% glyphosate salt (38.3% glyphosate acid equivalent), 34.7% polyvinylpyrrolidone and 23.1% filler.

The coherent solid was cut into flakes and the dispersion time for a sample of 0.60 mm thickness as measured by the standard test method was 172 seconds.

EXAMPLE 3

The procedure of Example 1 was repeated using potassium glyphosate (4.0 g of an aqueous solution containing 55.1% salt—45% glyphosate acid equivalent), ethanol (12.5 g), polyvinylpyrrolidone (4.0 g; molecular weight 10,000) and CALFLO E (3.0 g). The constituents were mixed to form a viscous slurry which was cast onto a polymer film (polythene) substrate using a 'doctor blade' set at a blade height of 1 mm. The cast slurry was dried for 45 minutes in an oven maintained at 50° C. and fragmented during drying to form flakes.

The resulting flakes contained 23.9% glyphosate salt (19.6% glyphosate acid equivalent), 43.5% polyvinylpyrrolidone and 32.6% filler.

The dispersion time as measured by the standard test method for a 0.30 mm thick sample was 60 seconds.

EXAMPLE 4 and 5

The procedure of Example 1 was repeated using isopropylamine glyphosate (10.4 g of an aqueous solution containing 60.7% salt—45% glyphosate acid equivalent), methanol (12.5 g), polyvinylpyrrolidone (4.0 g; molecular weight 44,000) and CALFLO E (3.0 g).

The above was repeated except that the solvent methanol was replaced by 12.5 g of glacial acetic acid (Example 5).

The resulting solids contained 47.4% glyphosate salt (40% of glyphosate acid equivalent), 30.1% polyvinylpyrrolidone and 22.5% filler.

The dispersion times as measured by the standard test method were 60 seconds (Example 4: sample thickness 0.36 mm) and 85 seconds (Example 5: sample thickness=0.30 mm).

EXAMPLE 6

The procedure of Example 1 was repeated using glyphosate trimesium (13.8 g of an aqueous solution containing 60.5% salt—41.7% acid equivalent), ethanol (11.7 g), polyvinylpyrrolidone (3.0 g; molecular weight 44,000) and AEROSIL 200 (3.3 g) (silica powder, surface area 200 $m^2$/g. AEROSIL is a trade mark of Degussa AG, Germany).

The resultant solid contained 57.0% glyphosate salt (39.3% glyphosate acid equivalent), 20.5% polyvinylpyrrolidone and 22.5% filler.

A good coherent solid was obtained which dispersed in 120 seconds as measured using the standard test method.

EXAMPLE 7

The procedure of Example 1 was repeated except that the filler CALFLO E was replaced by Microtalc filler (3.3 g) (hydrated magnesium silicate with a mean particle size of approximately 7 $\mu$m).

The resultant solid was coherent and flexible and dispersed in 87 seconds as measured using the standard test method.

EXAMPLE 8

AGRIMER VA6 (5 g, a copolymer of vinlyacetate/vinylpyrrolidone in a molar ratio 60/40 (AGRIMER is a trade mark of ISP (Great Britain) Co. Ltd.) was added to ethanol (12.5 g) and stirred manually until the polymer had dissolved. A high surface area calcium silicate filler CALFLO E (2.5 g) and glyphosate trimesium (6.0 g) were added to the polymer solution and mixed using a high speed mechanical stirrer over a period of 5 minutes until a homogenous, viscous slurry was produced.

The viscous film-forming medium was tape cast onto a polymer film (polythene) substrate using a "doctor blade" set at a blade height of 1 mm. The cast tape was dried for 45 minutes in an oven maintained at 50° C. and then stripped from the substrate as a coherent sheet which was subsequently subdivided into flakes.

The resultant solid contained 32.6% glyphosate salt (22.5% glyphosate acid equivalent), 44.9% copolymer and 22.5% filler.

The dispersion time as measured by the standard test method for a 0.39 mm thick sample was 160 seconds.

Comparison 2

The formulation procedure described in the above example was repeated with the exception that the ethanol was replaced with CIPAC Standard Hard Water D (11.7 g; 342 ppm hardness, $Ca^{2+}$: $Mg^{2+}$=4:1). The water, polymer and filler produced a homogenous mixture as before. However, addition of the water soluble salt (glyphosate trimesium active ingredient) resulted in the formation of a two-phase system which was not possible to homogenise. The mixture consisted of a liquid phase and an elastic-like solid phase. It was not possible to cast this mixture.

EXAMPLE 9

The procedure of Example 1 was repeated using hydroxpropyl cellulose (2.0 g) as film-forming polymer, glacial acetic acid (12.0 g) as solvent, CALFLO E (1.0 g) and glyphosate trimesium (3.5 g of an aqueous solution containing 60.5% glyphosate salt—41.7% glyphosate acid equivalent).

The coherent solid obtained was very flexible and contained 41.4% glyphosate salt (28.5% glyphosate acid equivalent), 39.1% hydroxpropyl-cellulose and 19.5% filler.

The dispersion time as measured by the standard test method for a 0.26 mm thick sample was 320 seconds.

Comparison 3

The formulation procedure described in the above example was repeated with the exception that the glacial acetic acid was replaced with CIPAC Standard Hard Water D (11.7 g; 342 ppm hardness, $Ca^{2+}$:$Mg^{2+}$=4:1). The water, polymer and filler produced a homogenous mixture as before. However, addition of the water soluble salt (glyphosate trimesium active ingredient) resulted in the formation of a two-phase system which was not possible to homogenise. The mixture consisted of a liquid phase and an elastic-like solid phase. It was not possible to cast this mixture.

EXAMPLE 10

The procedure of Example 1 was repeated using glyphosate trimesium (54.5 g of an aqueous solution containing 60.5% glyphosate salt—41.7% glyphosate acid equivalent), ethanol (12.5 g), polyvinylpyrrolidone (3.0 g; molecular weight 44,000) and CALFLO E (8.0 g).

The resulting solid contained 75.0% glyphosate salt (51.7% glyphosate acid equivalent), 6.8% polyvinylpyrrolidone and 18.2% filler.

The dispersion properties of the solid were excellent.

EXAMPLE 11

The procedure of Example 1 was repeated using glyphosate trimesium (15.4 g of an aqueous solution containing 60.5% glyphosate salt—41.7% glyphosate acid equivalent), ethanol (18.0 g), polyvinylpyrrolidone (8.0 g; molecular weight 24,000), CALFLO E (4.0 g) and AL2042 (5.3 g of an aqueous 70% w/w solution of alkyl polyglycoside. AL2042 is a trade mark of Imperial Chemical Industries).

The resultant coherent, non-dusty solid contained 37.2% glyphosate salt (25.7% glyphosate acid equivalent), 32.0% polyvinylpyrrolidone, 16.0% filler and 14.8% AL2042. The dispersion time as measured by the standard test method for a 0.69 mm thick sample was 150 seconds.

EXAMPLE 12

AGRIMER VA6 (1.1 g) was added to ethanol (4.0 g) and stirred manually until the polymer had dissolved. Ammonium glyphosate (22 g of an aqueous solution containing 40% by weight glyphosate acid equivalent and a molar ratio of ammonia to glyphosate acid of 1.75:1.00), glycerol (0.2 g), AEROSOL OT-B (0.1 g, sodium dioctylsulphosuccinate (85%) and sodium benzoate (15%); AEROSOL is a trademark of American Cyanamid Company) and CALFLO E (2.7 g) were added to the polymer solution and mixed manually until a homogeneous, viscous slurry was produced.

The viscous film-forming medium was tape cast onto a polymer film (Polythene) as substrate using a "doctor blade"

set at a blade height of 1 mm. The cast tape was dried for 45 minutes in an oven maintained at 50° C. and then stripped from the substrate as a coherent sheet which was subsequently subdivided into flakes. The thickness and density of the flakes were 0.5 mm and 1.02 gcm$^{-3}$ respectively.

When a sample of flakes (4.62 g) was exposed to ambient conditions (27° C. –29° C. temperature, 35–57% relative humidity) in an open petri dish for 24 hours, it did not deliquesce. The weight gain due to moisture pick-up under these conditions was 1.5% in a sample which had been pre-dried for 24 hours in an oven maintained at 50° C.

EXAMPLE 13

Polyvinylpyrrolidone (4.0 g, molecular weight 24,000) was added to ethanol (6.0 g) and stirred manually until the polymer had dissolved. Paraquat dichloride (20.0 g of an aqueous solution comprising 32.11% salt) and CALFLO E (3.3 g) were added to the polymer solution and mixed until a homogeneous, viscous slurry was produced.

The viscous film-forming medium was tape cast onto a polymer film (Melinex) as substrate using a "doctor blade" set at a blade height of 1 mm. The cast tape was dried for 2 hours in an oven maintained at 50° C. until a dry solid was obtained.

The tape cast product contained 46% paraquat dichloride and dissolved and dispersed readily in water.

EXAMPLE 14

Polyvinylpyrrolidone (247 g, molecular weight 8,000) was added to ethanol (577 g) and stirred until the polymer had dissolved. CALFLO E (165.4 g) and glyphosate trimesium {513.2 g of an aqueous solution comprising 60.5% salt (41.5% by weight acid equivalent )} were added to the polymer solution and mixed using a mechanical stirrer at a speed of 400 rpm, over a period of 5 minutes until a homogeneous, viscous slurry was produced.

The viscous slurry was then diluted with water until the rheology of the slurry was suitable for processing in a spray drier (approximately 90 g of water was added to 200 g of slurry). The slurry was spray-dried using a pilot plant Niro atomiser with a two fluid nozzle. The inlet temperature was 135° C. and the outlet temperature was 69° C. The nozzle nitrogen pressure was 40 psi and the material was pumped at 19 ml per minute. The material was collected at both the bottom of the dryer and in the fines collection jar. 42 g of fines and 23 g of coarse granules were collected. The dried granules were white in colour, had good flow properties and did not stick to the wall of the dryer. The granules were easily wetted in water and readily dispersed and dissolved upon mild agitation.

EXAMPLE 15

The procedure of Example 1 was repeated using ethanol (35 g), polyvinylpyrrolidone (15.0 g), CALFLO E (10.0 g) and glyphosate trimesium {42.4 g of an aqueous solution containing 60.5% salt (41.7% glyphosate acid equivalent)}. The resultant coherent solid contained 50.6% salt (34.9% by weight acid equivalent).

The solid was dissolved in water and the resultant solution showed good efficacy when tested against standard plant species in a glasshouse.

What is claimed is:

1. A process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer (b) a water soluble material which is non film-forming and (c) a water-miscible solvent in which the film-forming polymer is soluble and thereafter (ii) drying the film-forming aqueous medium to form the solid composition; wherein the film-forming polymer is a polyvinylpyrrolidone, a polyvinyl alcohol, a partially hydrolyzed polyvinyl acetate, a modified polyvinylpyrrolidone, a vinylpyrrolidone copolymer, a polyethylene oxide, an ethylene/maleic anhydride copolymer, a methyl vinyl ether-maleic anhydride copolymer, a water-soluble cellulose, a water-soluble polyamide, a water-soluble polyester, a copolymer of acrylic acid, a homopolymer of acrylic acid, a starch, a natural gum, a protein, or a mixture of any two or more thereof.

2. A process for producing a solid, water-soluble or water-dispersible composition comprising a non film-forming material supported by a film-forming polymer wherein the supported material is a water-soluble material, which process comprises (i) preparing a film-forming aqueous medium containing (a) a film-forming polymer, (b) a water soluble material which is non film-forming, (c) a water-miscible solvent in which the film-forming polymer is soluble and (d) a solid filler and thereafter (ii) drying the film-forming aqueous medium to form the solid composition.

3. A process according to claim 2 wherein the solid filler is calcium silicate, magnesium silicate, sodium aluminium silicate, silica, mica, a cellulosic fibre, starch or a diatomaceous earth.

4. A process according to claim 3 wherein the solid filler has a surface area greater than 80 m$^2$/g.

5. A process according to claim 1 wherein the water-soluble material which is not film-forming is a strong electrolyte.

6. A process according to claim 1, wherein the water soluble material which is non film-forming is an inorganic salt, a salt of glyphosate, a bipyridylium salt, glufosinate or fomesafen.

7. A process according to claim 1 wherein the film-forming polymer is a polyvinylpyrrolidone or vinylpyrrolidone copolymer and the water-miscible solvent is a linear or branched chain primary or secondary alcohol containing from 1 to 6 carbon atoms, ethylene glycol, propionic acid, methylcyclohexanone, methylene dichloride, N-methyl-2-pyrrolidone, or diethanolamine.

8. A process according to claim 7 wherein the solvent is ethanol.

9. A process according to claim 1, wherein the film-forming polymer is carboxycellulose and the water-miscible solvent is glacial acetic acid.

10. The process of claim 1, wherein the modified polyvinylpyrrolidone is a polyvinylpyrrolidone/vinyl acetate copolymer; wherein the vinylpyrrolidone copolymer is a vinylacetate/vinylpyrrolidone copolymer; wherein the water-soluble cellulose is hydroxypropylcelluolose, carboxycellulose or carboxymethylcellulose; wherein the natural gum is an alginate or a dextrin; and wherein the protein is a gelatin or a casein.

11. The process of claim 6, wherein the inorganic salt is ammonium sulphate; wherein the salt of glyphosate is a trimesium salt of glyhposate, a trimethylsulphonium salt of glyphosate, an isopropylamine salt of glyphosate, a sodium salt of glyphosate, a potassium salt of glyphosate, or an ammonium salt of glyphosate; and wherein the bipyridylium salt is paraquat dichloride.

12. The process of claim 1, wherein the water soluble material which is non film-forming is an electrolyte of an agrochemical, an electrolyte of an agrochemical adjuvant or a mixture thereof.

13. The process of claim 1, wherein the film-forming aqueous medium further comprises a plasticizer, a surfactant, an antifoam agent, a viscosity aid, or a mixture of two or more thereof.

14. The process of claim 2, wherein the film-forming polymer is a polyvinylpyrrolidone, a polyvinyl alcohol, a partially hydrolyzed polyvinyl acetate, a modified polyvinylpyrrolidone, a vinylpyrrolidone copolymer, a polyethylene oxide, an ethylene/maleic anhydride copolymer, a methyl vinyl ether-maleic anhydride copolymer, a water-soluble cellulose, a water-soluble polyamide, a water-soluble polyester, a copolymer of acrylic acid, a homopolymer of acrylic acid, a starch, a natural gum, a protein, or a mixture of any two or more thereof.

15. The process of claim 14, wherein the modified polyvinylpyrrolidone is a polyvinylpyrrolidone/vinyl acetate copolymer; wherein the vinylpyrrolidone copolymer is a vinylacetate/vinylpyrrolidone copolymer; wherein the water-soluble cellulose is hydroxypropylcelluolose, carboxycellulose or carboxymethylcellulose; wherein the natural gum is an alginate or a dextrin; and wherein the protein is a gelatin or a casein.

16. The process of claim 2, wherein the water-soluble material which is non film-forming is a strong electrolyte.

17. The process of claim 2, wherein the water soluble material which is non film-forming is an electrolyte of an agrochemical, an electrolyte of an agrochemical adjuvant or a mixture thereof.

18. The process of claim 2, wherein the water soluble material which is non film-forming is an inorganic salt, a salt of glyphosate, a bipyridylium salt, glufosinate or fomesafen.

19. The process of claim 18, wherein the inorganic salt is ammonium sulphate; wherein the salt of glyphosate is a trimesium salt of glyhposate, a trimethylsulphonium salt of glyphosate, an isopropylamine salt of glyphosate, a sodium salt of glyphosate, a potassium salt of glyphosate, or an ammonium salt of glyphosate; and wherein the bipyridylium salt is paraquat dichloride.

20. The process of claim 2, wherein the film-forming aqueous medium further comprises a plasticizer, a surfactant, an antifoam agent, a viscosity aid, or a mixture of two or more thereof.

21. The process of claim 1, wherein the solid composition comprises more than 60% by weight of the water soluble material which is non film-forming.

22. The process of claim 2, wherein the solid composition comprises more than 60% by weight of the water soluble material which is non film-forming.

23. The process of claim 2, wherein the film-forming polymer is a polyvinylpyrrolidone or vinylpyrrolidone copolymer and the water-miscible solvent is a linear or branched chain primary or secondary alcohol containing from 1 to 6 carbon atoms, ethylene glycol, propionic acid, methylcyclohexanone, methylene dichloride, N-methyl-2-pyrrolidone, or diethanolamine.

24. The process of claim 23, wherein the solvent is ethanol.

* * * * *